(12) United States Patent
Androvandi

(10) Patent No.: US 10,369,157 B1
(45) Date of Patent: Aug. 6, 2019

(54) MULTI-AGENT FORMULATION

(71) Applicant: Mauricio Androvandi, Barquisimeto (VE)

(72) Inventor: Mauricio Androvandi, Barquisimeto (VE)

(73) Assignee: MFKC 200, LLC, Doral, FL (US)

( * ) Notice: Subject to any disclaimer, the term of this patent is extended or adjusted under 35 U.S.C. 154(b) by 0 days.

(21) Appl. No.: 15/940,141

(22) Filed: Mar. 29, 2018

(51) Int. Cl.
*A61K 31/5517* (2006.01)
*A61P 43/00* (2006.01)
*A61K 31/4168* (2006.01)
*A61K 31/4468* (2006.01)
*A61K 31/135* (2006.01)
*A61K 9/00* (2006.01)

(52) U.S. Cl.
CPC ........ *A61K 31/5517* (2013.01); *A61K 9/0019* (2013.01); *A61K 31/135* (2013.01); *A61K 31/4168* (2013.01); *A61K 31/4468* (2013.01); *A61P 43/00* (2018.01)

(58) Field of Classification Search
CPC .................... C07D 233/56; A61K 31/5517
See application file for complete search history.

(56) References Cited

U.S. PATENT DOCUMENTS

| | | | |
|---|---|---|---|
| 5,635,204 A * | 6/1997 | Gevirtz | A61K 9/7084 424/447 |
| 6,264,981 B1 | 7/2001 | Zhang et al. | |
| 8,513,198 B2 | 8/2013 | Ellis et al. | |
| 8,653,033 B2 | 2/2014 | Ellis et al. | |
| 8,765,680 B2 | 7/2014 | Ellis et al. | |
| 2014/0296830 A1 | 10/2014 | Gibson et al. | |
| 2016/0067175 A1 | 3/2016 | Blaise | |
| 2016/0263105 A1* | 9/2016 | Blaise | A61K 31/485 |

OTHER PUBLICATIONS

Lasky et al., Anesth. Analg, 2012, 115:1155-61.*

* cited by examiner

*Primary Examiner* — Rei Tsang Shiao
(74) *Attorney, Agent, or Firm* — Malloy & Malloy, PL

(57) ABSTRACT

A multi-agent formulation for intravenous administration comprising an active component and an inert carrier solution. The active component comprises a plurality of constituents, including at least a sleep inducing agent, an analgesic agent, an anesthetic agent, and an adrenergic agonist agent. The sleep inducing agent comprises Midazolam, the analgesic agent comprises Fentanyl, the anesthetic agent comprises Ketamine, and the adrenergic agonist agent comprises Clonidine. The active component comprises the following amounts, indicated as a percentage of the weight of the active component: approximately 4.75% of the sleep inducing agent, approximately 0.10% of the analgesic agent, approximately 95.08% of the anesthetic agent, and approximately 0.07% of the adrenergic agonist agent.

2 Claims, No Drawings

MULTI-AGENT FORMULATION

BACKGROUND OF THE INVENTION

Field of the Invention

The present invention relates to a multi-agent formulation and a method for administering an anesthetic and/or a sedative to a patient.

Description of the Related Art

Compounds are known for use in surgical procedures to induce a state of anesthesia in a patient. Other compounds are known for use as sedatives and/or analgesics. Although such compounds exist, none are a truly complete formulation which may provide a variety of benefits in a surgical or other related procedure. Therefore, there is a need for a formulation that achieves a useful balance between sedation and anesthesia. Significant benefits may be realized by providing a formulation comprising a variety of constituents that synergistically provide a patient several beneficial effects including at least sedation, analgesia, and anesthesia. A further benefit may be realized by providing a formulation which may be used as either a sedative or an anesthetic according to the specific dosage administered to the patient. The industry may also benefit from a formulation which, in addition to imparting sedation and/or anesthesia, imparts analgesic properties in the patient for a substantial period of time following a surgical or other medical procedure.

SUMMARY OF THE INVENTION

The present invention is directed to a multi-agent formulation which may be administered to a patient at least as an anesthetic and/or sedative, depending on the specific dose administered to the patient. Accordingly, the present multi-agent formulation may be used to impart a variety of different effects in a patient. The present multi-agent formulation comprises an active component that itself comprises a plurality of constituents. Specifically, in one embodiment of the present invention, the active component comprises a sleep inducing agent. In one embodiment, a sleep inducing agent may be a derivative of the imidazobenzodiazepine group. In another embodiment of the present invention, the active component comprises an analgesic agent. In one embodiment, an analgesic agent may be an opioid agonist. In another embodiment of the present invention, the active component comprises an anesthetic agent. In one embodiment, an anesthetic agent may be a cyclohexanone derivative. In another embodiment of the present invention, the active component comprises an adrenergic agonist agent. In one embodiment, an adrenergic agonist agent may be an imidazoline derivative, such as Clonidine.

When administered at dosages as a sedative, the present multi-agent formulation allows the patient to substantially maintain spontaneous respiration. Conversely, when the present multi-agent formulation is administered as an anesthetic, intubation may be necessary. When a dosage of the multi-agent formulation is administered to a patient, the plurality of constituents, provided in the amounts disclosed herein, provides the patient with a useful balance between sedation and anesthesia. The analgesic effect of the present multi-agent formulation following the underlying procedure may last up to six hours, with a relatively short recovery period.

The quantities of the constituents of the present multi-agent formulation may vary. In one embodiment of the present invention, a standard unit dosage of the multi-agent formulation comprises an amount of a sleep inducing agent of approximately 0.125 milligrams ("mg") to approximately 1 mg. In another embodiment of the present invention, a standard unit dosage of the multi-agent formulation comprises an amount of an analgesic agent of approximately 2.5 micrograms ("μg") to approximately 20 μg. In yet another embodiment of the present invention, a standard unit dosage of the multi-agent formulation comprises an amount of an anesthetic agent of approximately 2.5 milligrams ("mg") to approximately 20 mg. In a further embodiment of the present invention, a standard unit dosage of the multi-agent formulation comprises an amount of an adrenergic agonist agent of approximately 1.875 micrograms ("μg") to approximately 15 μg.

For distribution purposes, in at least one embodiment, the present multi-agent formulation is packaged in 20 milliliter ("ml") vials. More in particular, in one embodiment, a 20 ml vial of the present multi-agent formulation comprises approximately 2.5 mg to approximately 20 mg of a sleep inducing agent. In another embodiment, a 20 ml vial of the present multi-agent formulation comprises approximately 50 μg to approximately 400 μg of an analgesic agent. A 20 ml vial of the present multi-agent formulation, in yet another embodiment, comprises approximately 50 mg to approximately 400 mg of an anesthetic agent. In one further embodiment, a 20 ml vial of the present multi-agent formulation comprises approximately 37.5 μg to approximately 300 μg of an adrenergic agonist agent.

In one embodiment of the present invention, an active component of the present multi-agent formulation comprises approximately 1% to approximately 10% of a sleep inducing agent, by weight. In another embodiment of the present invention, an active component comprises approximately 0.01% to approximately 5% of an analgesic agent, by weight. In another embodiment of the present invention, an active component comprises approximately 90% to approximately 98% of an anesthetic agent, by weight. In a further embodiment of the present invention, an active component comprises approximately 0.01% to approximately 5% of an adrenergic agonist agent, by weight.

The present invention is also directed to a method of administering the present multi-agent formulation. Generally, one or more of the constituents of an active component of the present multi-agent formulation may be mixed with each other. In one embodiment of the multi-agent formulation according to the present invention, one or more of the constituents of the inventive formulation may be mixed into an inert carrier solution. In one embodiment of the present invention, an "initial therapeutically effective dosage" of the multi-agent formulation is the initial dosage that induces a "state of sedation" in a patient. In another embodiment of the present invention, the "initial therapeutically effective dosage" of the multi-agent formulation is the initial dosage that induces a "state of anesthesia" in a patient. When administered as a sedative, the "initial therapeutically effective dosage" will generally induce a "state of sedation" in a patient that may last approximately 10 minutes to approximately 15 minutes. In one embodiment of the present invention, a "subsequent therapeutically effective dosage" of the multi-agent formulation is a quantity of the formulation, which will substantially maintain a "state of sedation" in a patient. In another embodiment of the present invention, a "subsequent therapeutically effective dosage" of the multi-agent formulation is a quantity of the formulation, which will substantially maintain a "state of anesthesia" in a patient. Generally, the "subsequent therapeutically effective dosage" may be approximately 30% of the "initial therapeutically effective dosage."

These and other objects, features and advantages of the present invention will become clearer when the detailed description is taken into consideration.

DETAILED DESCRIPTION

The present invention is directed to a multi-agent formulation to be used as an anesthetic and/or a sedative, and to a corresponding method of administering the formulation to a patient. In one embodiment, the multi-agent formulation of the present invention is intended to be administered intravenously to the patient. It is also within the scope of the present invention that the patient be a human being, but it is also possible to administer the present multi-agent formulation to different species of animals.

Several embodiments of the present invention are described below, with reference to examples for illustrative purposes only. The specific details provided herein are intended to provide a comprehensive understanding of the present invention. The present invention, however, may be practiced without some of the specific details presented herein, and/or with different methods or procedures. The order of the examples presented herein is not limiting as such examples may be practiced or performed in a different order.

Unless otherwise defined, all of the terms of art, notations, nomenclature, and/or scientific terms are intended to have the commonly understood meaning in the relevant art. Some terms, which may have a commonly understood meaning, are nonetheless defined for clarity and/or ease of reference. Such inclusions do not necessarily represent a substantial difference over the meaning of the term in the relevant industry. Moreover, terms such as those defined in commonly used dictionaries, should be construed to carry a meaning consistent with the meaning of the terms in the relevant industry, and/or as defined herein.

Indefinite articles such as "a," "an" and "the" include plural reference unless the context clearly indicates otherwise. Unless specifically indicated otherwise, the singular shall include the plural and vice versa. The phrase "and/or," as used herein, should be understood to mean "either or both" of the elements so conjoined, that is, elements that may be conjunctively present in some cases and disjunctively present in others. As used herein, "or" shall have the same meaning as "and/or" as defined above. The terms "including," "includes," "having," "has," "with," or variants thereof, are intended to be inclusive, such as the term "comprising."

As used herein, the term "anesthesia" refers to the absence of all sensation, including sensitivity to pain, induced by an anesthetic constituent, agent, or substance.

As used herein, the terms "anesthetic" and "anesthetic agent" are interchangeable and shall mean any compound, pharmaceutical, drug, agent, or constituent that is capable of inducing a "state of anesthesia" in a patient. A "state of anesthesia," as used herein, refers to at least a partial, and in some cases a complete, loss of feeling in a patient. The term "general anesthesia" as used herein refers to the absence of sensation and consciousness as induced by various anesthetic agents, constituents, or other compounds which may include analgesia, amnesia, muscle relaxation, and unconsciousness.

As used herein, the term "sedation" refers to at least a partial loss of sensation, including sensitivity to pain, induced by an anesthetic constituent, agent, or substance.

A "sedative" and "sedative agent," as used herein, shall include any compound, pharmaceutical, drug, agent, or constituent that is capable of inducing a "state of sedation" in a patient. The term "state of sedation" as used herein refers to at least a partial loss of feeling in a patient, wherein the patient may maintain a spontaneous respiration without the need for assisted respiration or intubation.

The term "formulation," as used herein, shall mean and include a combination, mixture, solution, or collection of agents, components or constituents selected for their beneficial properties.

The term "inert carrier solution," as used herein, shall mean an agent used to dissolve a formulation, substance, or pharmaceutical compound. The term "inert carrier solution" further refers to an agent that comprises little or no therapeutic properties by itself, and which has been sterilized for administration to a patient.

As used herein, the term "patient" refers to any type of animal, including a human being, which is the recipient of a particular treatment.

The terms "administration," "administer," and "administering," as used herein, refer to providing a dosage or other quantity of a formulation to a patient. The term "intravenous administration" refers to providing a dosage or other quantity of a formulation directly into the vein of a patient. The present multi-agent formulation may be administered to a patient alone, but may also be applied in combination with other compounds, excipients, fillers, binders, carriers, or other related vehicles of administration. Thus, administration of the present multi-agent formulation may be by way of suitable carriers and/or vehicles. Suitable carriers and/or vehicles should render the present multi-agent formulation amenable to intravenous administration. Examples of suitable carriers and/or vehicles include injectable solutions such as sterile aqueous or non-aqueous solutions, or saline solutions; suspensions, emulsions, micro-emulsions, or nano-emulsions; micelles; synthetic polymers; microspheres; nano-particles, and other related carriers and/or vehicles.

A "standard unit dosage" as used herein, shall mean an amount of an active component required to induce and/or maintain either a "state of anesthesia" or a "state of sedation," as defined herein, per 10 kilograms of body weight of a patient.

A "therapeutically effective dosage," as used herein, refers to an amount of the present multi-agent formulation necessary to render the desired therapeutic result in a patient. Specifically, a "therapeutically effective dosage" of the present multi-agent formulation shall be sufficient to induce and/or maintain either a "state of anesthesia" or a "state of sedation," as defined herein. Further, the "therapeutically effective dosage" shall also be sufficient to treat, cure, or otherwise alleviate other symptoms for which the present multi-agent formulation may be administered.

More specifically, as used herein, an "initial therapeutically effective dosage" refers to the quantity of the formulation required to induce either a "state of anesthesia" or a "state of sedation" in a patient.

Also as used herein, a "subsequent therapeutically effective dosage" refers to an amount of the multi-agent formulation required to maintain either the "state of sedation" or the "state of anesthesia" in the patient.

The term "disorder," as used herein, refers to a disease, condition, or other departure from healthy or normal biological activity, which may impair normal function.

The term "underlying procedure," as used herein, refers to a medical procedure, surgical procedure, or other treatment which requires inducing and/or maintaining either a "state of sedation" or a "state of anesthesia" in order to be performed in a patient.

Formulation

A multi-agent formulation according to at least one embodiment of the present invention comprises an active component. An active component may have one or more constituents or agents. In one embodiment of the present invention, an active component of a multi-agent formulation comprises a sleep inducing agent, which may be a derivative of the imidazobenzodiazepine group. In another embodiment of the present multi-agent formulation, an active component comprises an analgesic agent, which may be an opioid agonist. In one further embodiment of the present multi-agent formulation, an active component comprises an anesthetic agent, which may be a cyclohexanone derivative. An active component in yet another embodiment of the present multi-agent formulation comprises an adrenergic agonist agent, which may be an imidazoline derivative. The foregoing constituents, namely, a sleep inducing agent, an analgesic agent, an anesthetic agent, and an adrenergic agonist agent, each comprise beneficial properties that achieve a useful balance between sedation and anesthesia. More specifically, administration of the present multi-agent formulation comprising one or more of the foregoing constituents, achieves a substantial synergic effect, which acts on the central nervous system of a patient in several different ways influencing the ability to regulate neuronal activity.

When the present multi-agent formulation is administered as a sedative, the natural reflexes of a patient remain substantially unaffected. In turn, the airways of the patient remain substantially protected and unobstructed because the patient is capable of maintaining spontaneous respiration. In one embodiment of the present invention, a therapeutically effective dosage of the multi-agent formulation may be administered to induce a "state of sedation" providing an analgesic effect which may last approximately 6 hours after the underlying procedure. In another embodiment of the present invention, a therapeutically effective dosage of the multi-agent formulation may be administered to induce a "state of anesthesia" providing an analgesic effect which may also last approximately 6 hours after the underlying procedure. There is a relatively small recovery period after administration of a therapeutically effective dosage of the present multi-agent formulation. Depending on the underlying procedure and condition of a patient, it may be possible for the patient to stand approximately 30 minutes after administration of a therapeutically effective dosage of the present multi-agent formulation.

It is within the scope of the present invention that the present multi-agent formulation be used either as an anesthetic and/or as a sedative depending on what is required for the procedure to be performed on the patient. Accordingly, the present multi-agent formulation may be used in a wide range of medical procedures or interventions. The following are non-limiting examples of medical procedures or interventions in which the present multi-agent formulation may be used: debridement and/or skin grafts in burn patients; neurodiagnostic interventions and spinal taps; auricular, nasal, buccal, or other related interventions; sigmoidoscopies and other related rectal procedures; cardiac catheterization interventions; hemodynamic procedures and placement of pacemakers; orthopedic interventions including removal of osteosynthesis material and other related orthopedic interventions, closed fracture reductions and minor amputations; obstetrical interventions of relatively short duration, such as, uterine curettages, biopsies, cyst exertion, exophytic lesion treatment and HPV cryogenic treatments, hysteroscopies, and salpingographies; dental procedures which may require sedation; dental treatments that require sedation; conscious sedation for intensive care procedures; ophthalmologic interventions as a surgical treatment of cataracts, pterygium, and substantially all other eye procedures where intraocular pressure is not compromised.

An active component in accordance with the present invention comprises one or more constituents provided in quantities that may vary. Specifically, in one embodiment of the present invention, a standard unit dosage of a multi-agent formulation comprises approximately 0.125 mg to approximately 1.0 mg of the sleep inducing agent. In another embodiment of the present invention, a standard unit dosage of a multi-agent formulation comprises approximately 2.5 µg to approximately 20.0 µg of the analgesic agent. In a further embodiment of the present invention, a standard unit dosage of a multi-agent formulation comprises approximately 2.5 mg to approximately 20 mg of the anesthetic agent. In yet one further embodiment of the present invention, a standard unit dosage of a multi-agent formulation comprises approximately 1.875 µg to approximately 15.0 µg.

For distribution purposes, the present multi-agent formulation may be packaged in a 20 milliliter (ml) vials. In one embodiment, a 20 ml vial of the present multi-agent formulation comprises approximately 2.5 mg to approximately 20 mg of a sleep inducing agent. In another embodiment, a 20 ml vial of the present multi-agent formulation comprises approximately 50 µg to approximately 400 µg of an analgesic agent. A 20 ml vial of the present multi-agent formulation, in one further embodiment, comprises approximately 50 mg to approximately 400 mg of an anesthetic agent. In yet one other embodiment, a 20 ml vial of the present multi-agent formulation comprises approximately 37.5 µg to approximately 300 µg of an adrenergic agonist agent.

In one embodiment, an active component of the present multi-agent formulation comprises approximately 1% to approximately 10% of a sleep inducing agent, by weight. In another embodiment, an active component of the present multi-agent formulation comprises approximately 0.01% to approximately 5% of an analgesic agent, by weight. In one further embodiment, an active component of the present multi-agent formulation comprises approximately 90% to approximately 98% of an anesthetic agent, by weight. In one other embodiment, an active component of the multi-agent formulation comprises approximately 0.01% to approximately 5% of an adrenergic agonist agent, by weight.

In one embodiment, an active component of the present multi-agent formulation comprises approximately 4% to approximately 7% of a sleep inducing agent, by weight. In another embodiment of the present multi-agent formulation, an active component comprises approximately 0.05% to approximately 2% of an analgesic agent, by weight. In still one further embodiment of the present multi-agent formulation, the active component comprises approximately 93% to approximately 96% of an anesthetic agent, by weight. In a yet another embodiment of the present multi-agent formulation, an active component comprises approximately 0.05% to approximately 2% of an adrenergic agonist agent, by weight.

Favorable results have been observed with the present multi-agent formulation comprising the following amounts of the various constituent. In one embodiment, an active component of the present multi-agent formulation comprises approximately 4% to approximately 5% of a sleep inducing agent, by weight. In another embodiment, an active component of the multi-agent formulation comprises approximately 0.08% to approximately 0.12% of an analgesic agent, by weight. In another embodiment, an active component of the present multi-agent formulation approximately 95% to approximately 96% of an anesthetic agent, by weight. In a further embodiment, an active component comprises approximately 0.06% to approximately 0.08% of an adrenergic agonist agent, by weight.

Favorable results have also been observed with a formulation comprising the following constituent amounts. In one embodiment, an active component of the present multi-agent formulation comprises approximately 4.75% of a sleep inducing agent, by weight. In a further embodiment, an active component of the present multi-agent formulation comprises approximately 0.1% of an analgesic agent, by weight. In another embodiment, an active component of the present multi-agent formulation comprises approximately 95.08% of an anesthetic agent, by weight. In a further embodiment, an active component of the present multi-agent formulation comprises approximately 0.07% of an adrenergic agonist agent, by weight.

Pharmacological Properties

Sleep Inducing Agent

In one embodiment of the present invention, the multi-agent formulation comprises a sleep inducing agent, such as, a fast acting sleep inducing agent, which may be a derivative of the imidazobenzodiazepine group. A sleep inducing agent according to the present invention may comprises a free base which is a lipophilic substance that is not very soluble in water. Specifically, the basic nitrogen in the second position of the ring's structure of the imidazobenzodiazepine, allows the active ingredient of the sleep inducing agent to form water-soluble salts with acids. The pharmacological action of the sleep inducing agent is characterized by short duration due to rapid metabolic transformation. The sleep inducing agent, in at least one embodiment, produces a sedative, and somniferous, effect of pronounced intensity, as well as an anxiolytic, anticonvulsive and myorelaxant effect. By way of example only, a sleep inducing agent according to the present invention may comprise Midazolam, which has the chemical formula $C_{18}H_{13}C_1FN_3$ and the International Union of Pure and Applied Chemistry (IUPAC) name 8-chloro-6-(2-fluorophenyl)-1-methyl-4H-imidazo[1,5-a][1,4]benzodiazepine.

Analgesic Agent

In one embodiment of the present invention, the formulation comprises an analgesic agent. The analgesic agent may be an opioid agonist generally used for pain management, and which may have a rapid onset and generally short lasting effects. As a non-limiting example, an analgesic agent according to the present invention may comprise Fentanyl, which has the chemical formula $C_{22}H_{28}N_2O$ and the chemical IUPAC name N-phenyl-N-[1-(2-phenylethyl) piperidin-4-yl]propanamide, which is a potent narcotic analgesic, and which may be used by itself or in conjunction with an anesthetic. The analgesic agent according to the present invention may maintain cardiac stability and, when administered at relatively high doses, may prevent the onset of hormonal changes associated with stress. The potency of the analgesic agent should be roughly equivalent to over one hundred (100) times the potency of morphine. For example, the potency of 1 µg of the analgesic agent may be roughly equivalent to 0.125 mg of morphine. Similarly, and also by way of example, the potency of 100 µg of the analgesic agent should be roughly equivalent to 12.5 mg of morphine. It should be noted that the inventive formulation should be administered in the quantities which are described hereinafter in detail, which may vary according to different factors, and not necessarily in a single dosage comprising 100 µg of the analgesic agent, a quantity which is only provided to illustrate the relative potency of the analgesic agent according to the present invention. Even though an analgesic agent, such as Fentanyl, may have a relatively quick onset, it may take several minutes for its effects to become appreciable. These effects include respiratory depression and/or an increased analgesic effect in a patient. When applied intravenously, a therapeutically effective dosage of the analgesic agent should provide the patient with an analgesic effect that may generally last for approximately 30 minutes, depending on the weight of the patient. Nevertheless, the residual effects of the analgesic agent may last for up to approximately four (4) hours while the patient's organism metabolizes the analgesic agent. The strength of the analgesic agent varies according the potency of the dose, which may be adjusted according to the severity of the pain associated with the specific underlying procedure. By way of example only, when Fentanyl is used in rats, the minimum ratio of DL50 to DE50 is 277, versus 69.5 and 4.6 in the case of morphine and pethidine, respectively. As with other narcotic analgesics, and depending on the dose and the rate of administration, the analgesic agent, may cause muscular rigidity, euphoria and/or bradycardia. Histamine release and skin tests in humans, as well as in vivo tests in dogs, demonstrate that a significant clinical amount of histamine is rarely released after administration of Fentanyl. The effects of the analgesic agent may be substantially reversed through administration of a narcotic antagonist such as, but not limited to, Naloxone.

Anesthetic Agent

The present invention may also comprise an anesthetic agent. In at least one embodiment, an analgesic agent which may be a non-barbiturate, relatively fast acting, anesthetic which may induce several effects in a patient. These effects may include a substantially profound state of analgesia, a substantially normal laryngopharyngeal reflex, and/or a substantially normal to a lightly augmented musculoskeletal tone. The anesthetic agent according to one embodiment of the present invention also produces a substantially mild cardiorespiratory stimulation, although sometimes it may produce respiratory depression. In one embodiment, an anesthetic agent comprises a cyclohexanone derivative. In one embodiment, an anesthetic agent comprises a cyclohexanone derivative. The anesthetic agent may comprise Ketamine, which has the chemical formula $C_{13}H_{16}ClNO$ and the chemical IUPAC name 2-(2-chlorophenyl)-2-(methylamino)cyclohexan-1-one.

An anesthetic agent according to the present invention may produce sedation, immobility, amnesia and should provide the patient with a substantial analgesic effect. The anesthetic state produced an anesthetic agent according to the present invention may be referred to as "dissociative anesthesia" given that it should selectively interrupt cerebral association tracts before producing a somesthetic sensory block. The anesthetic agent according to the present invention may also selectively depress the thalamus-neocortical system before significantly blocking the limbic and reticular activator systems. For example, numerous hypotheses exist that attempt to explain the effects of an anesthetic agent such as Ketamine. These hypotheses include binding to N-methyl-D-aspartate receptors (NMDA receptors) in the central nervous system, interaction with central and spinal opiate receptors, and interaction with cholinergic receptors of muscarinic, norepinephrine and serotonin. Activity on NMDA receptors may be responsible for analgesia as well as the psychiatric effects (psychosis) of the anesthetic agent. The anesthetic agent according to the present invention should comprise sympathomimetic activity, leading to tachycardia, hypertension, increased cerebral and myocardial oxygen consumption, increased cerebral blood flow, and increased intraocular and intracranial pressure. In addition, the anesthetic agent should be a potent bronchodilator. For example, clinical effects observed on patients following Ketamine administration include increased blood pressure, increased muscle tone (may resemble catatonia), opening of the eyes (usually accompanied by nystagmus), and increased myocardial oxygen consumption.

Adrenergic Agonist Agent

In one embodiment of the present invention, the present multi-agent formulation may comprise an adrenergic agonist agent which may be an antihypertensive agent. The adrenergic agonist agent may be a receptor agonist, derivative of the imidazoline group. The adrenergic agonist agent according to the present invention should essentially act on the central nervous system, resulting in at least partially reduced sympathetic efferences and a decrease in peripheral resistance, renal vascular resistance, heart rate and blood pressure. Administration of the adrenergic agonist agent according to the present invention should generally result in a substantially unaffected renal blood flow and glomerular filtration rate. Further, administration of the adrenergic agonist agent according to the present invention should result in substantially normal postural reflexes, thus, orthostatic symptoms should be relatively infrequent and substantially mild when manifested. Long-term treatment and/or administration of the adrenergic agonist agent according to the present invention, should result in a cardiac output that tends to return to relatively normal values, while peripheral resistance should remain reduced. As an example, a decrease in pulse rate has been observed in most patients treated with Clonidine. The adrenergic agonist agent according to the present invention, however, should not alter the normal hemodynamic response to exercise. In one embodiment according to the present invention, the adrenergic agonist agent may comprise Clonidine, which has the chemical formula $C_9H_9C_{12}N_3$ and the chemical IUPAC name N-(2,6-dichlorophenyl)-4,5-dihydro-1H-imidazol-2-amine. In another embodiment of the present invention, the adrenergic agonist agent may alternatively comprise Dexmedetomidine, which has the chemical formula $C_{13}H_{16}ClN_2$, and the chemical IUPAC name 5-[(1S)-1-(2,3-dimethylphenyl)ethyl]-1H-imidazole. Dexmedotomidine is a selective agonist of adrenergic alpha-2 receptors, and which is similar to Clonidine, but which has an increased affinity towards adrenergic alpha-2 receptors. Further, Dexmedotomidine has a sedative effect which may be enabled by inhibition of the locus coeruleus, a nucleus of the brain stem.

Pharmacokinetic Properties

Sleep Inducing Agent

Intravenous administration of a sleep inducing agent according to the present invention should result in a distribution of the plasma concentration over time that has two phases. The volume of distribution at steady state should be approximately 0.7 to approximately 1.2 liters per kg. Approximately 96% to approximately 98% of the sleep inducing agent should bind to plasma proteins, mostly due to albumin. As an illustrative example, in humans it has been demonstrated that Midazolam may slowly pass through the placenta and thereby enter fetal circulation. Also as an example, small amounts of Midazolam have been found in human milk.

As to the metabolism associated with the sleep inducing agent according to the present invention, it should is almost completely eliminated by biotransformation. For example, approximately 30% to approximately 60% of the sleep inducing agent should be extracted by the liver. Additionally, the sleep inducing agent should be hydroxylated by the isoenzyme 3A4 of the cytochrome P450. The major urinary and plasma metabolite of the sleep inducing agent should be alpha-hydroxymidazolam. Plasma concentrations of alpha-hydroxymidazolam should represent approximately 12% of those of the parent compound of the sleep inducing agent. Alpha-hydroxymidazolam should be pharmacologically active but should contribute only to lesser, only approximately 10%, of the effects of the sleep inducing agent according to the present invention when administered intravenously.

Regarding the ability of relatively healthy individuals to eliminate the sleep inducing agent from their system, the elimination half-life of the sleep inducing agent should be approximately 1.5 hours to approximately 2.5 hours. The plasma clearance should be approximately 300 ml to approximately 500 ml per minute. The sleep inducing agent should be eliminated via the kidneys (approximately 60% to approximately 80% of the administered dose), and should be generally recovered as glucuroconjugated alpha-hydroxymidazolam. Less than approximately 1% of the dose should be recovered though urine as unmodified drug. The elimination half-life of the alpha-hydroximidazolam should be less than approximately 1 hour. When the sleep inducing agent is administered intravenously, its elimination kinetics should not substantially differ from that of a bolus injection.

Analgesic Agent

Serum levels of the analgesic agent according to the present invention should rapidly decline after intravenous administration. The half-lives of the distribution phases should be approximately 1 minute and approximately 18 minutes respectively. The plasma protein binding of the analgesic agent should be approximately 84%. The analgesic agent should have a central compartment volume of distribution of approximately 13 liters, and a total volume of distribution in equilibrium of approximately 339 liters. The analgesic agent should be metabolized rapidly, especially in the liver. The analgesic agent should have a clearance of approximately 574 ml per minute. Approximately 75% of the administered dose of the analgesic agent should be eliminated in roughly 24 hours and only approximately 10% of the dose should be eliminated as an unmodified drug. The terminal elimination half-life should be approximately 475 minutes. The analgesic agent may have a reduced clearance in the elderly and in weakened patients, which may result in a longer terminal half-life. In patients with renal or hepatic dysfunction, the analgesic agent clearance may be altered by changes in plasma proteins and metabolic clearance, which in turn may lead to an increased serum concentration.

Anesthetic Agent

The anesthetic agent should be rapidly absorbed after parenteral administration. The anesthetic agent may easily cross the placental barrier, and may be easily distributed on highly irrigated tissues, such as the heart, lungs, and brain. Thereafter, the anesthetic agent may be distributed on muscle and peripheral tissue, and then on adipose tissue. The distribution phase should last approximately 45 minutes with a half-life of approximately 10 minutes to approximately 15 minutes, which clinically corresponds to the drug's anesthetic effect. Approximately one hour after administration, the maximum plasma concentration of the anesthetic agent should reach an average value of approximately 0.75 μg per ml and CSF levels of approximately 0.2 micrograms (μg) per 1 ml. The anesthetic agent should undergo a process of hepatic N-demethylation (through the cytochrome P450 system) and hydroxylation of the cyclohexanone ring, with the formation of water-soluble conjugates that are excreted through urine. Subsequently, the anesthetic agent should undergo an oxidation process, with the formation of a cyclohexanone derivative. The unconjugated N-demethylated metabolite should have an activity that is approximately 6 times lesser than that of the anesthetic agent itself. The unmixed cyclohexanone demethylated derivative has an activity that should be approximately 10 times lesser than that of the anesthetic agent itself. The anesthetic agent should have a half-life of approximately 2 hours to approximately 3 hours. For example, studies in humans suggest that approximately 91% of the dose of Ketamine is recovered through urine while approximately 3% is recovered through excreted feces.

Adrenergic Agonist Agent

The pharmacokinetics of the adrenergic agonist agent should be proportional to the specific dose if within a range of approximately 75 μg to approximately 300 μg. The adrenergic agonist agent should be well absorbed by the human body. As a non-limiting example, Clonidine, is well absorbed by the human body and has a lesser initial effect. Peak plasma concentrations of the adrenergic agonist agent should be reached in approximately 1 hour to approximately 3 hours after oral administration. Plasma protein binding of the adrenergic agonist agent should be approximately 30% to approximately 40%. Distribution of the adrenergic agonist agent in tissues should be relatively wide and quick. The adrenergic agonist agent may pass through the blood-brain barrier, as well as the placental barrier, and should be generally excreted in breast milk. Nevertheless, there is insufficient information regarding the effect of adrenergic agonist agents, such as Clonidine, on newborns. The terminal elimination half-life of the adrenergic agonist agent should range from approximately 5 hours to approximately 25.5 hours. The terminal elimination half-life of the adrenergic agonist agent may be prolonged up to 41 hours in patients with severe impairment of renal function. Approximately 70% of the administered dose of the adrenergic agonist agent should be eliminated through urine, with approximately 40% to approximately 60% of the original drug being substantially unaltered. Additionally, the major metabolite of the adrenergic agonist agent should be pharmacologically inactive. For example, the major metabolite of Clonidine is p-hydroxyclonidine, which is pharmacologically inactive. Approximately 20% of the total administered amount of the adrenergic agonist agent should be excreted through feces. The pharmacokinetics of the adrenergic agonist should not be affected by the diet or ethnicity of the patient. In patients with substantially normal renal function, the adrenergic agonist's antihypertensive effect is achieved with plasma concentrations of approximately 0.2 nanograms per 1 ml to approximately 2.0 nanograms per 1 ml.

The following are non-limiting examples of the present multi-agent formulation and are not to be interpreted as limiting the scope of the present invention.

EXAMPLES

The following examples are illustrative of the amounts of the individual constituent(s), which may be present in a standard unit dosage of the multi-agent formulation according to the present invention. By way of example, one (1) standard unit dosage may be included in approximately 1 ml of the multi-agent formulation according to the present invention, which includes the amount of the plurality of constituents and of a sufficient amount of an inert carrier solution to amount to approximately 1 ml of total volume. Also as an example, because the present multi-agent formulation may be delivered in 20 ml vials, it is within the scope of the present invention that each 20 ml vial should comprise approximately twenty (20) standard unit dosages of the present multi-agent formulation. Similarly, 20 ml of the present multi-agent formulation includes the amount of the plurality of constituents and of a sufficient amount of an inert carrier solution to amount to approximately 20 ml of total volume. The values shown in Example 3 are recommended for a relatively healthy patient, but it is within the scope of the present invention that these values may be adjusted for every patient taking into account his or her weight, age, existing or previous medical condition(s) and/or treatment(s), and other related factors.

Example 1

| Constituent | Standard Unit Dosage (Approx.) |
| --- | --- |
| Sleep Inducing Agent | 0.125 mg |
| Analgesic Agent | 2.5 μg |
| Anesthetic Agent | 2.5 mg |
| Adrenergic Agonist Agent | 1.875 μg |

Example 2

| Constituent | Standard Unit Dosage (Approx.) |
| --- | --- |
| Sleep Inducing Agent | 0.25 mg |
| Analgesic Agent | 5 μg |
| Anesthetic Agent | 5.0 mg |
| Adrenergic Agonist Agent | 3.75 μg |

Example 3

| Constituent | Standard Unit Dosage (Approx.) |
| --- | --- |
| Sleep Inducing Agent | 0.5 mg |
| Analgesic Agent | 10 μg |
| Anesthetic Agent | 10.0 mg |
| Adrenergic Agonist Agent | 7.5 μg |

Example 4

| Constituent | Standard Unit Dosage (Approx.) |
| --- | --- |
| Sleep Inducing Agent | 1.0 mg |
| Analgesic Agent | 20 μg |
| Anesthetic Agent | 20.0 mg |
| Adrenergic Agonist Agent | 15.0 μg |

Method of Administration

The multi-agent formulation according to the present invention may be manufactured as an injectable solution. In one embodiment according to the present invention, the multi-agent formulation may be prepared at ambient temperature, such as, for example, from approximately 60° Fahrenheit to approximately 90° Fahrenheit. In one embodiment according to the present invention, one or more constituents may be provided in the proportions described herein to create an active component. For intravenous administration purposes, an active component may be combined or mixed with an inert carrier solution. During the preparation, care should be taken to ensure that the active component and/or the inert carrier solution should be adequately handled to avoid contamination. Further, containers, injectors, and all other attendant equipment should also be sterilized prior to mixing and administering the present multi-agent formulation. As is often the case with anesthetics, a patient's response after administration of the present multi-agent formulation depends, among several factors, on his or her weight, age, physical condition or existing illnesses, the underlying disorder or condition, and any concomitant use of other medications. Thus, for administration purposes, the specific quantities of the present multi-agent formulation may vary accordingly.

As used herein, the "initial therapeutically effective dosage" is the recommended amount of the present multi-agent formulation to be administered to a patient to induce either a "state of anesthesia" or a "state of sedation." For the purposes of inducing a "state of sedation," the "initial therapeutically effective dosage" will provide the patient substantially all of the beneficial properties of the present multi-agent formulation, and further, the patient will be able to substantially maintain a spontaneous respiration. For the purposes of inducing a "state of sedation" in the patient, the "initial therapeutically effective dosage" is approximately equivalent to one (1) standard unit dosage of the present multi-agent formulation, and roughly corresponds to approximately 10 kg of body weight of the patient. Thus, for the purposes of inducing a "state of sedation" in the patient, the "initial therapeutically effective dosage," which corresponds to approximately 10 kg of body weight of the patient, and may be included in approximately 1 ml of the present multi-agent formulation, which comprises an active component, and sufficient volume of an inert carrier solution to amount to approximately 1 ml of volume. By way of example only, approximately 10 ml of the present multi-agent formulation, comprising approximately ten (10) standard unit dosages, should be administered to a patient weighting approximately 100 kg, each ml comprising approximately one (1) standard unit dosage that corresponds to approximately 10 kg of body weight of the patient.

Such "initial therapeutically effective dosage" will induce in the patient a "state of sedation" that will generally last from approximately 10 minutes to approximately 15 minutes. After initial administration, it may generally take approximately 60 seconds for the present multi-agent formulation to deliver its sedative effects. These effects generally include loss of consciousness and the desired analgesic effect required to perform the underlying procedure, which may be a relatively minor surgery or a related treatment. In order to maintain the effects of the present multi-agent formulation, a "subsequent therapeutically effective dosage" should be administered to the patient approximately every 15 minutes, and this may be continued for an hour, or longer. For sedation purposes, the "subsequent therapeutically effective dosage" should be from approximately 20% to approximately 40% of the "initial therapeutically effective dosage." Favorable results may be achieved with a "subsequent therapeutically effective dosage" that is approximately 30% of the "initial therapeutically effective dosage." By way of example only, in order to maintain a "state of sedation" in a 100 kilogram patient, approximately three (3) standard unit dosages of the present multi-agent formulation should be administered to the patient. Also by way of example, 3 ml of the present multi-agent formulation may be administered to the patient to maintain a "state of sedation," which includes the amount of the plurality of constituents and a sufficient amount of an inert carrier solution to amount to approximately 3 ml of total volume.

For the purposes of inducing a state of anesthesia, the "initial therapeutically effective dosage" should be approximately one and a half (1.5) to approximately two (2) times a standard unit dosages, as described herein. As a non-limiting example, in order to induce a state of anesthesia in a patient weighting approximately 100 kilograms, approximately 15 ml to approximately 20 ml of the present multi-agent formulation may be administered to the patient. Also as an example, approximately fifteen (15) to approximately twenty (20) standard unit dosages of the present multi-agent formulation, such as in approximately 15 ml to approximately 20 ml of the present multi-agent formulation including the amount of the plurality of constituent and an inert carrier solution, should be administered to a patient weighting approximately 100 kilograms in order to induce a state of anesthesia. After administration of the "initial therapeutically effective dosage," it may take approximately 45 seconds to approximately 60 seconds for the multi-agent formulation to deliver its initial anesthetic effects. After approximately 90 seconds to approximately 120 seconds of administration of the "initial therapeutically effective dosage," the patient will generally demonstrate adequate conditions for intubation for respiratory assistance. It is recommended that neuromuscular relaxants be given to the patient for more efficient and safe nasotracheal or orotracheal intubation.

The method according to the present invention comprises providing a multi-agent formulation including an inert carrier solution and an active component as described above. For the purposes of inducing a "state of anesthesia," the method according to the present invention comprises intravenously administering to the patient an "initial therapeutically effective dosage" of the present multi-agent formulation. The method according to the present invention further comprises administering to the patient a "subsequent therapeutically effective dosage" of the present multi-agent formulation to maintain the "state of anesthesia." The "subsequent therapeutically effective dosage" may be generally administered to the patient after a predetermined period of time following administration of the "initial therapeutically effective dosage" of the multi-agent formulation. Thereafter, the "state of anesthesia" may be maintained by administering to the patient a further "subsequent therapeutically effective dosage" of the multi-agent formulation once every predetermined period of time. The predetermined period of time generally comprises approximately 10 minutes to approximately 15 minutes. For the purpose of inducing a "state of anesthesia," the "subsequent therapeutically effective dosage" should similarly be from approximately 20% to approximately 40% of the "initial therapeutically effective dosage." Favorable results may also be achieved with a "subsequent therapeutically effective dosage" that is approximately 30% of the "initial therapeutically effective dosage."

For the purposes of inducing a "state of sedation," the method according to the present invention comprises intravenously administering to a patient an "initial therapeutically effective dosage." For the purposes of inducing a "state of sedation," the "initial therapeutically effective dosage" may be roughly equivalent to one (1) standard unit dosage, but may be varied according the characteristics of the patient such as, but not limited to, size, weight, age, underlying conditions or disorders, current and/or prior use of other medications, etc. Thus, in some embodiments of the present invention, the "initial therapeutically effective dosage" may be increased or decreased as much as 50%. For example, in one embodiment of the present invention, the "initial therapeutically effective dosage" comprises approximately 1.5 standard unit dosages, such as in approximately 1.5 ml of the present multi-agent formulation. In another embodiment, the "initial therapeutically effective dosage" comprises approximately one half (½) of a standard unit dosage, such as in approximately 0.5 ml of the present multi-agent formulation.

The method according to the present invention further comprises administering to the patient a "subsequent therapeutically effective dosage" to maintain the "state of sedation." The "subsequent therapeutically effective dosage" may be generally administered to the patient after a predetermined period of time following administration of the "initial therapeutically effective dosage" of the multi-agent formulation. Thereafter, the "state of sedation" may be maintained by administering to the patient a further "subsequent therapeutically effective dosage" of the multi-agent formulation once every predetermined period of time. This predetermined period of time also comprises a span of approximately 10 minutes to approximately 15 minutes.

Special Considerations

Adverse cardiorespiratory events have rarely occurred, namely respiratory depression, apnea, respiratory arrest and cardiac arrest. These events are more likely to occur when the multi-agent formulation is administered at a faster rate and/or higher dose than recommended. Children younger than approximately 6 months of age are particularly vulnerable to airway obstruction and hypoventilation. Therefore, in children under 6 months of age, it is recommended to administer only a substantially reduced initial therapeutically effective dosage, and to continue to administer a subsequent therapeutically effective dosage(s) in substantially reduced increments until the desired clinical effect is achieved.

Regarding the effects of the present multi-agent formulation after the patient exits either the "state of anesthesia" or "state of sedation," approximately 60% of the patients generally experience a pleasant dream state, feelings of joy, dissociative or other floating feelings. Some patients as a view this as an overall pleasant experience. The duration of these effects usually does not exceed a few hours after exiting the "state of anesthesia" or "state of sedation." These effects may be at least partially reduced by minimizing the verbal and tactile stimulation to the patient during the anesthetic recovery period.

Interaction with Other Pharmaceuticals

The multi-agent formulation according to the present invention, given that its several constituents provide diverse beneficial effects, is a substantially complete anesthetic formulation. Other than perhaps in conjunction with a muscle relaxant, which may be beneficial under certain circumstances, the present multi-agent formulation may be administered by itself. A muscle relaxant may be beneficial in some instances, for orotracheal and/or nasotracheal intubation. No negative effects have been observed when the present multi-agent formulation is used in conjunction with a muscle relaxant, or with halogenated gases. Each constituent of the present multi-agent formulation comprises its own set of pharmacodynamics properties. Thus, when the different constituents of the present multi-agent formulation interact with one another, they achieve a substantially complete balance between neuronal activity and analgesia. Consequently, the present multi-agent formulation does not need to be used in conjunction with an adjuvant, or other additional pharmaceutical substance or other compound.

Frequency of Adverse Reactions

It is noted that perhaps the most serious reaction following administration of the present multi-agent formulation is depression of the respiratory system. The degree of depression naturally depends on the potency of the dose being administered. The following nomenclature is used to represent the frequency in patients of adverse reactions which have been observed in patients following administration of the multi-agent formulation according to the present invention:

Very common (VC) ≥1 in 10
Common (C) ≥1 in 100, but <1 in 10
Uncommon (UC) ≥1 in 1,000, but <1 in 100
Rare (R) ≥1 in 10,000, but <1 in 1,000
Very Rare (VR) <1 in 10,000
Unknown (U) cannot be estimated from the available data

| CONDITION | FREQUENCY |
|---|---|
| Immune System Disorders | |
| Anaphylactic Reaction | (VR) |
| Psychiatric Disorders | |
| Drowsiness, Vivid Dreams | (C) |
| Agitation, Delirium Depression | (UC) |
| Nervous System Disorders | |
| Headache, dizziness, and nystagmus | (VC) |
| Involuntary and clone movements | |
| Eye Disorders | |
| Diplopia | (C) |
| Cardiac Disorders | |
| Tachycardia | (C) |
| Bradycardia, arrhythmia | (R) |
| Vascular Disorders | |
| Hypertension, hypotension, vasodilation | (C) |
| Respiratory, Thoracic and Mediastinal Disorders | |
| Respiratory depression | (C) |
| Apnea | (R) |
| Gastrointestinal Disorders | |
| Nausea, vomiting, constipation | (VC) |
| Dyspepsia and dry mouth | (UC) |
| Skin and Subcutaneous Tissue Disorders | |
| Pruritus, erythema | (VC) |
| Skin and Subcutaneous Tissue Disorders | |
| Sweating | (C) |
| Rash and phlebitis at the administration location | (UC) |
| Renal and Urinary Disorders | |
| Urinary retention | (UC) |
| General Disorders | |
| Reactions at the injection site | (UC) |
| Feeling cold | (UC) |

In the event of an overdose resulting from administration of the present multi-agent formulation, its depressant effects will be substantially increased. This may induce apnea and/or lead to a consequent cardiac arrest. Thus, it is once more recommended to closely monitor the vital functions of the patient during administration of the present multi-agent formulation.

Since many modifications, variations and changes in detail can be made to the described preferred embodiment of the invention, it is intended that all matters in the foregoing description and shown in the accompanying drawings be interpreted as illustrative and not in a limiting sense. Thus, the scope of the invention should be determined by the appended claims and their legal equivalents.

What is claimed is:

1. A standard unit dosage per 10 kilograms of a patient's body weight of a multi-agent formulation for inducing a state of sedation and/or a state of anesthesia in the patient comprising:

approximately 0.5 mg of 8-chloro-6-(2-fluorophenyl)-1-methyl-4H-imidazo[1,5a][1,4] benzodiazepine, approximately 10 µg of N-phenyl-N-[1-(2-phenylethyl)piperidin-4-yl]propanamide, approximately 10 mg of 2-(2-chlorophenyl)-2-(methylamino)cyclohexan-1-one, and approximately 7.5 µg of N-(2,6-dichlorophenyl)-4,5-dihydro-1H-imidazol-2-amine.

2. A multi-agent formulation for inducing a state of sedation and/or a state of anesthesia in a patient, said formulation comprising:

an active component comprising approximately 4.75% by weight of 8-chloro-6-(2-fluorophenyl)-1-methyl-4H-imidazo[1,5a][1,4] benzodiazepine, approximately 0.1% by weight of N-phenyl-N-[1-(2-phenylethyl)piperidin-4-yl]propanamide, approximately 95.08% by weight of 2-(2-chlorophenyl)-2-(methylamino)cyclohexan-1-one, approximately 0.07% by weight of N-(2,6-dichlorophenyl)-4,5-dihydro-1H-imidazol-2-amine, and an inert carrier solution.

* * * * *